United States Patent
Thomas et al.

(10) Patent No.: US 7,041,099 B2
(45) Date of Patent: May 9, 2006

(54) INTRAOPERATIVE ENDOCARDIAL AND EPICARDIAL ABLATION PROBE

(75) Inventors: Stuart Thomas, Wentworthville (AU); David Ross, Cheltenham (AU); Arianwen Rees, Seaforth (AU); Robert Patterson, Faulconbridge (AU); Michael Daly, Eastwood (AU); Ilija Koevski, Toongabbie (AU)

(73) Assignee: Western Sydney Area Health Service, New South Wales (AU)

(*) Notice: Subject to any disclaimer, the term of this patent is extended or adjusted under 35 U.S.C. 154(b) by 254 days.

(21) Appl. No.: 10/396,231

(22) Filed: Mar. 24, 2003

(65) Prior Publication Data

US 2004/0030331 A1    Feb. 12, 2004

Related U.S. Application Data

(62) Division of application No. 09/485,361, filed as application No. PCT/AU98/00590 on Jul. 24, 1998, now Pat. No. 6,540,742.

(30) Foreign Application Priority Data

Jul. 24, 1997    (AU) ........................... PO8208

(51) Int. Cl.
*A61B 18/14*    (2006.01)

(52) U.S. Cl. .................... 606/41; 607/99; 607/105; 607/113; 607/122

(58) Field of Classification Search ............ 606/41, 606/45, 46, 49; 607/99, 105, 113, 122
See application file for complete search history.

(56) References Cited

U.S. PATENT DOCUMENTS

| | | | |
|---|---|---|---|
| 5,156,151 A | | 10/1992 | Imran |
| 5,462,545 A | * | 10/1995 | Wang et al. .................. 606/41 |
| 5,487,757 A | * | 1/1996 | Truckai et al. .............. 604/264 |
| 5,617,854 A | | 4/1997 | Munsif |
| 5,720,719 A | | 2/1998 | Edwards et al. |
| 5,810,802 A | | 9/1998 | Panescu et al. |
| 5,871,443 A | * | 2/1999 | Edwards et al. ............. 600/374 |
| 5,882,346 A | * | 3/1999 | Pomeranz et al. .......... 607/122 |
| 5,895,386 A | | 4/1999 | Odell et al. |
| 6,041,256 A | | 3/2000 | Michel |
| 6,071,282 A | | 6/2000 | Fleischman |
| 6,126,657 A | | 10/2000 | Edwards et al. |
| 6,146,379 A | | 11/2000 | Fleischman et al. |
| 6,161,543 A | | 12/2000 | Cox et al. |
| 6,592,581 B1 | * | 7/2003 | Bowe ......................... 606/41 |

FOREIGN PATENT DOCUMENTS

| | | |
|---|---|---|
| AU | 70522/96 | 10/1996 |
| WO | WO 93/20878 | 10/1993 |
| WO | WO95/15115 | 6/1995 |
| WO | WO97/06727 | 2/1997 |
| WO | WO97/18853 | 5/1997 |
| WO | WO97/33526 | 9/1997 |

* cited by examiner

*Primary Examiner*—Lee S. Cohen
(74) *Attorney, Agent, or Firm*—Merchant & Gould P.C.

(57) ABSTRACT

An elongate, malleable ablation probe including an elongate malleable body (38) and a plurality of longitudinally spaced apart electrodes (40) disposed at a distal end thereof. The electrodes (40) are separated one from another by insulative material. In one embodiment, a malleable insert is provided for insertion into a flexible longitudinal sleeve, the flexible longitudinal sleeve conforming to the shape of the malleable insert upon such insertion. In other embodiments, a malleable core is surrounded by a flexible body, the electrodes (40) being mounted to the body.

5 Claims, 8 Drawing Sheets

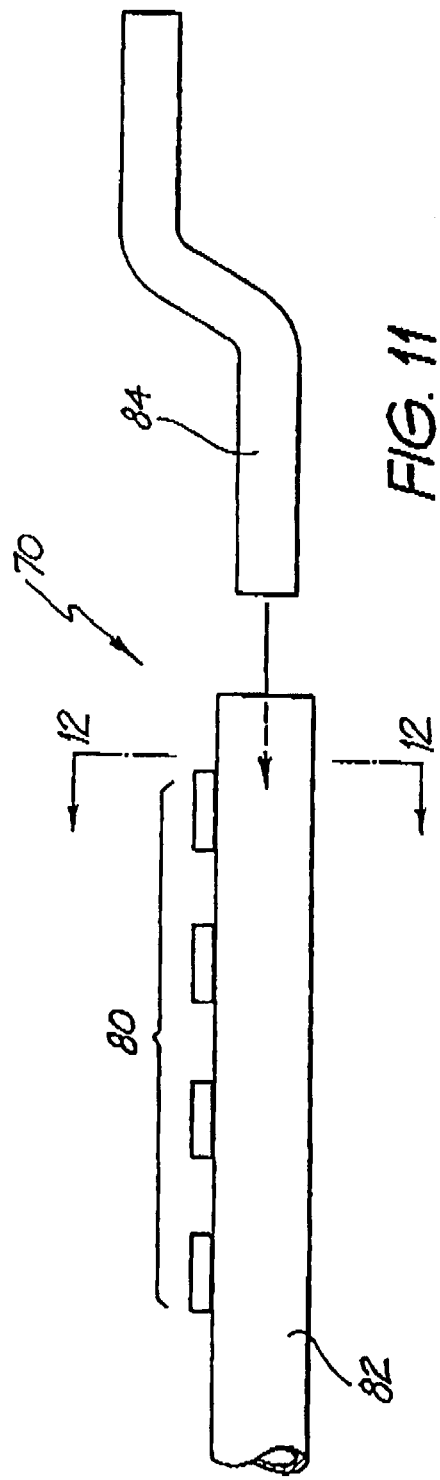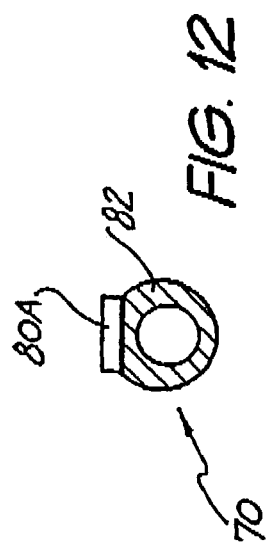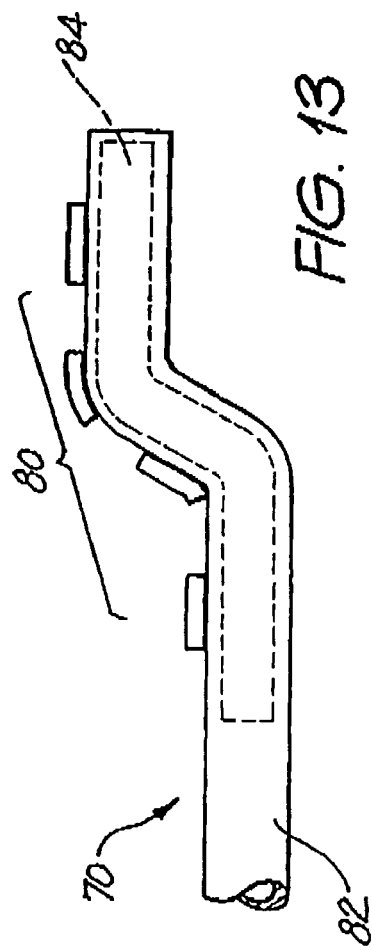

INTRAOPERATIVE ENDOCARDIAL AND EPICARDIAL ABLATION PROBE

The application is a divisional of application Ser. No. 09/485,361, filed Dec. 14, 2000, now U.S. Pat. No. 6,540,742 which is a 371 of PCT/AU98/00590, filed Jul. 24, 1998, which application(s) are incorporated herein by reference.

The present invention relates to a method and apparatus for mapping and ablating tissue, and in particular to a malleable, shapeable probe for producing elongated linear lesions in tissue.

BACKGROUND

It is known that tissue, including damaged myocardial tissue, can be ablated by the application of radio frequency energy thereto via conductive electrodes embodied in a probe structure. RF ablation of tissue is commonly used in an attempt to remove myocardial defects, tumours, portions of tissue mass, and the like. RF ablation can be used to treat cardial disfunctions such as ventricular arrhythmia, atrial flutter, atrial fibrillation, ventricular tachycardia and the like.

Such disorders involve abnormal heart muscles causing abnormal activity of the electrical signals that are generated to create muscle contraction. One result of this abnormal electrical activity in the atrial part of the heart muscle may be an irregular heartbeat. A common feature of atrial fibrillation is impaired atrial contraction. The heart beat rate may also be increased.

Electrode catheters are commonly used to effect RF ablation of tissue to remove or otherwise interrupt the abnormal electrical activity caused by defective myocardial tissue.

FIG. 1 is a schematic diagram illustrating such a catheter 10. The catheter 10 is typically made of a highly flexible plastic or rubber tube 14. At the distal end of the catheter body 14 are located a number of metal electrodes 12 for delivering RF energy. The conventional catheter probe utilises ring-like electrodes concentrically arranged around the catheter body 14. Alternatively, the catheter probe 10 alone or in combination with the ring-like electrodes may have a single electrode at the tip of the distal end of the catheter 10. The catheter body 14 includes a number of internal electrical conductors (not shown) connected to respective ones of the electrodes 12 at one end. The conductors can be connected at an opposite end of the catheter 10 to a source of RF energy and other equipment. The RF energy is delivered via the conductors to the electrodes 12.

In use, such a catheter probe 10 is inserted via an incision in a patient's body into a blood vessel, such as a vein, and the catheter is then manoeuvred through the blood vessel to the patient's heart. Thus, the electrodes 12 at the distal end of the catheter 10 can be inserted into an interior chamber of a patient's heart to ablate endocardial tissue. FIG. 2 is a simplified schematic diagram illustrating the catheter 10 disposed within a portion of an atrium 20. A defective portion of the myocardial tissue is detected by mapping electrical activity in the myocardial tissue, and then applying RF energy via one or more of the electrodes 12 adjacent to the defective portion.

A significant disadvantage of conventional catheter ablation is that, due to the very flexible nature of the catheter itself, it is difficult to accurately position and maintain the positioning of the electrodes relative to a portion of myocardial tissue. This is disadvantageous in that movement and imprecise placement of the catheter can result undesirably in the ablation or destruction of healthy tissue, while at the same time the tissue sought-to-be ablated may not have been ablated, thereby requiring further ablation.

As will be understood from FIG. 2, due to the readily flexible nature of the catheter body 14 and its limited ability to retain any particular form, the catheter 10 is difficult to position at a desired location, and often does not adequately conform to the tissue surface. As shown in FIG. 2, due to contact with a far wall of the atrium, the catheter body 14 flexes upwardly from its insertion at left into the atrial chamber and is then bent downwardly at its distal end by the irregularity 22 in the myocardial tissue of the atrium 20. Due to the way in which the catheter 10 is bent and its imprecise positioning, only a small portion of the distal end of the catheter 10 contacts the tissue at location 22. In fact, only a small portion of the third electrode contacts the defective, irregularly shaped tissue 22.

Another disadvantage of such catheter probes 10 is that they are directed to ablating focal defects, where only a portion of an electrode in contact with the tissue produces a "spot" or pointlike lesion in the tissue.

A further catheter ablation probe has been proposed using the same type of highly flexible catheter structure in combination with an external guide wire provided between the distal end and an intermediate point of the catheter probe. The guide wire can be tightened or released so as to control arcuate flexing of a sequence of band-like electrodes arranged along the catheter. However, this probe is also disadvantageous in that movement and placement of the catheter is still imprecise and the electrodes may not have good contact with irregular surfaces to be ablated. Still further, the ring-like electrodes of such a catheter probe also produce a "spot" or pointlike lesion in the tissue.

Thus, conventional catheter probes have a number of significant disadvantages. Firstly, the electrodes of the probe are directed to producing spot or pointlike lesions in tissue. Secondly, due to the highly flexible nature of the catheter body, it is difficult to manoeuvre and accurately position and retain the position of the electrodes of the catheter at any position. Thirdly, again due to the very flexible nature of the catheter typically made of soft, bendable plastic, or rubber like substances, the distal end of the catheter does not readily conform to irregularly shaped surfaces of tissue. Accordingly, a need clearly exists for a probe capable of overcoming one or more disadvantages of conventional devices.

SUMMARY OF THE INVENTION

In a first aspect, the present invention provides an elongate, malleable ablation probe including:
an elongate malleable body; and
a plurality of longitudinally spaced apart electrodes disposed at a distal end of said malleable body, said electrodes being separated one from another by insulative material.

Preferably, the electrodes are flat and are arranged linearly along said probe.

In a second aspect, the present invention provides a probe for ablating tissue, including:
an elongate, bendable body;
a plurality of substantially flat spaced apart electrodes linearly arranged along a longitudinal extent of said body and connected with a surface of said body;
insulative material separating said spaced apart electrodes one from another;
a plurality of electrical conductors, wherein at least one of said plurality of conductors is connected to each respective one of the plurality of electrodes; and a malleable core disposed within said elongate body, whereby said probe is deformable and is able to retain a shape formed by bending said probe.

In a third aspect, the present invention provides a probe for ablating of tissue, comprising:

a tubular body of bendable material defining an elongate cavity;

a plurality of flat electrodes linearly arranged along the longitudinal extent of said tubular body;

insulative portions separating said electrodes from each other;

a plurality of electrical conductors, at least one of which is connected with each respective one of said plurality of electrodes; and an insert member having a predefined shape for insertion into the elongate cavity of said tubular body, wherein said tubular body conforms to the predefined shape upon insertion of the insert member into the elongate cavity.

In a fourth aspect, the present invention provides a probe for ablating tissue, comprising:

an elongate body of bendable material, wherein said body has a substantially flat surface extending along a longitudinal extent of a distal end of said body;

a plurality of flat electrodes arranged in a linear configuration on said flat surface of said body in a predetermined spaced apart relationship to each other;

insulative material separating said flat electrodes one from another;

a plurality of conductors, wherein at least one conductor is connected with each respective one of said plurality of electrodes; and a malleable core formed in said body, wherein said probe is deformable.

Preferably, in each of the above aspects of the invention, one or more prongs are connected with each electrode, wherein the one or more prongs is used to puncture the body and is capable of being bent.

In a fifth aspect, the present invention provides a probe for ablating tissue, comprising:

a relatively rigid body;

at least one flat, elongate electrode formed in a surface of a distal portion of said rigid body; and at least one electrical conductor connected with said electrode for delivery of RF energy thereto.

Preferably, a temperature sensing devices is connected to at least one electrode. Still further, at least two conductors of the plurality of conductors are connected to the electrode, and one of the conductors comprises a thermocouple as the temperature sensing device.

Still further, in each of the above aspects, the body is preferably made of insulative material.

In a sixth aspect, the present invention provides a method of ablating tissue, said method comprising the steps of:

deforming an elongated, malleable ablation probe to conform to an irregular surface of said tissue, wherein said probe comprises a linear arrangement of flat electrodes separated one from another by insulative material along a longitudinal extent of said probe; and ablating said tissue using one or more of said electrodes contacting said tissue.

BRIEF DESCRIPTION OF THE DRAWINGS

Preferred embodiments of the invention are described hereinafter, by way of example only, with reference to the drawings, in which:

FIGS. 11, 12 and 13 are side elevation, cross-sectional front, and sectional, side elevation views of a third embodiment of an RF ablation probe according to the invention.

DETAILED DESCRIPTION

Overview

Figure 1:
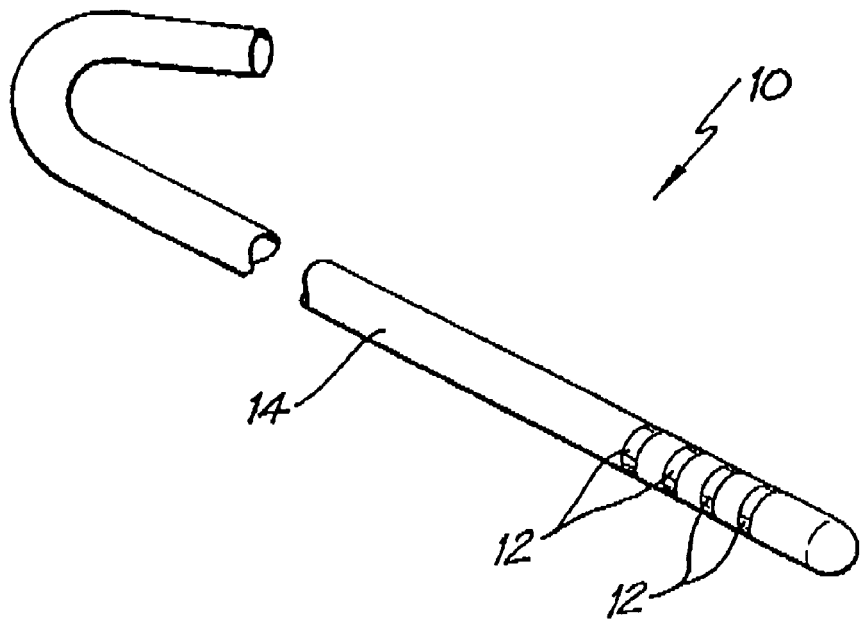
FIG. 1 is a perspective view of a conventional catheter probe.
Figure 2:
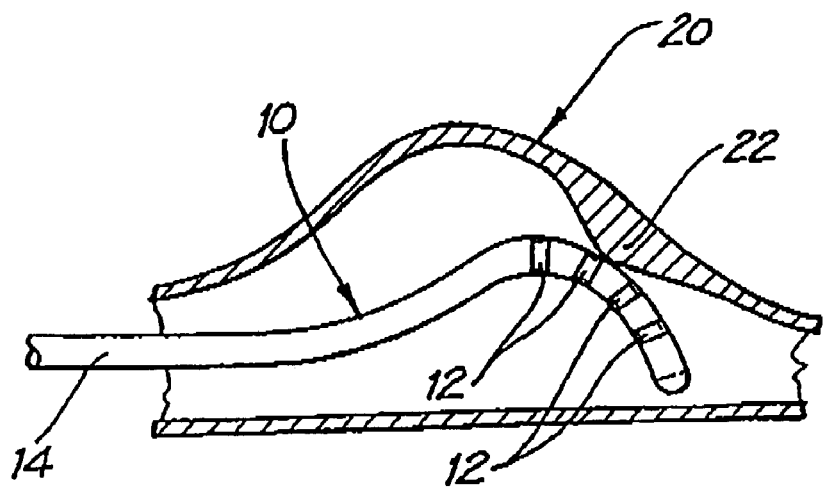
FIG. 2 is a side elevation view of the catheter probe of FIG. 1 during use.

The embodiments of the invention are directed to probes for ablating tissue to produce lesions, and in particular, to producing elongated linear lesions. The embodiments of the present invention are particularly useful for producing thin linear lesions of epicardial and endocardial tissue to septate the tissue, creating "corridors" to inhibit, minimise or eliminate reentrant pathways in such tissue. The first, second and third embodiments are particularly advantageous in that the probes have a structure enabling them to be readily and easily shaped to conform to the contour and/or irregularities of the surface of a tissue body.

The probe has a "memory" capability and will retain its shape when bent. In this way, the probe can be plastically deformed to substantially complement the shape of an irregular surface. In the following description, numerous specific details such as conductive materials for electrodes, specific types of tubing and fillers for probe bodies, specific malleable or plastically deformable materials for providing the above noted memory capability, etc. are described in detail to provide a more thorough description of the present invention. However, it will be apparent to one skilled in the art that the present invention may be practiced in other embodiments which do not employ the same specific details. Furthermore, well-known and understood aspects and features have not been described in detail so as not to unnecessarily obscure the present invention.

FIRST EMBODIMENT

A hand-held surgical device 34 incorporating a first embodiment radio frequency (RF) ablation probe according to the invention is illustrated in FIGS. 3 to 6. The probe has a malleable tip capable of being bent or deformed and maintaining the shaped configuration thus provided. To effect this, an elongate insulative body 38 of electrically and thermally insulative material is provided with a malleable core 44, preferably made of a soft metal such as copper and disposed within the insulative body 38.

A linear arrangement of spaced-apart flat electrodes 40 is disposed along the length of one surface of the elongated, insulative body 38 at its distal end. In the embodiment shown, the insulative body 38 is tubular in form and comprises flexible, bendable plastics or rubber material. One or more electrical leads or conductors 42 are connected to each of the electrodes 40 to deliver RF energy from a remote source. Preferably, the conductors 42 pass through the interior of the insulative probe body 38. Further, the electrical conductors 42 may be used to couple electrical signals from the electrodes to one or more remote devices connected at the opposite end of the probe, for example, to implement mapping of electrical activity in the myocardium.

This configuration and assembly of an RF ablation probe is particularly advantageous in that it is readily capable of being shaped and configured so that the linear arrangement of flat electrodes complements the contour and irregularities of a tissue body to be ablated. In particular, the probe can be readily shaped manually by a surgeon to conform to the surface of myocardial tissue and structures observed during surgery. The bendable, malleable characteristics of the RF ablation probe are provided by the malleable core member of the probe so that the probe is adaptable to variously shaped surfaces and has a memory capability to retain its formed shape.

Figure 4:
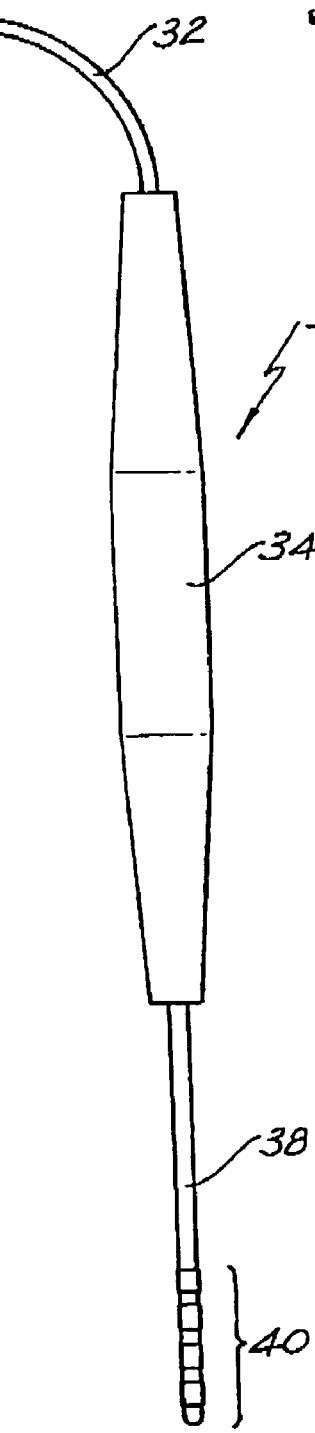
FIG. 4 is top plan view of the device of FIG. 3.

FIG. 4 illustrates a top plan view of the hand-held surgical device 30 including the probe structure 38 with the electrodes 40. The handle 34 is connected at one end by an electrical cable 32 to remote equipment (not shown), including an RF energy generator. Mapping equipment can also be connected to the probe. Temperature control equipment can also be connected to the probe for optimal functioning. The other end of the handle 34 has the adaptable malleable RF ablation probe 38, 40 extending therefrom. The probe body 38 has a number of the flat electrodes 40 linearly arranged in the upper surface thereof in a predetermined spaced apart relationship. Preferably, the probe has four rectangular flat electrodes 40. However, differing numbers of electrodes, e.g., 3, 5, etc, can be practiced without departing from the scope and spirit of the invention. The arrangement, shape and number of electrodes can be selected to produce elongated lesions of 1 to 10 cm. The long flat shape of the electrodes 40 maximises tissue contact while minimising the thermal momentum of each electrode. The small thickness and low mass of the electrodes 40 allow a respective temperature sensing device such as a thermistor or thermocouple associated with the electrode 40 to measure the true tissue temperature with relative accuracy.

Figure 3:
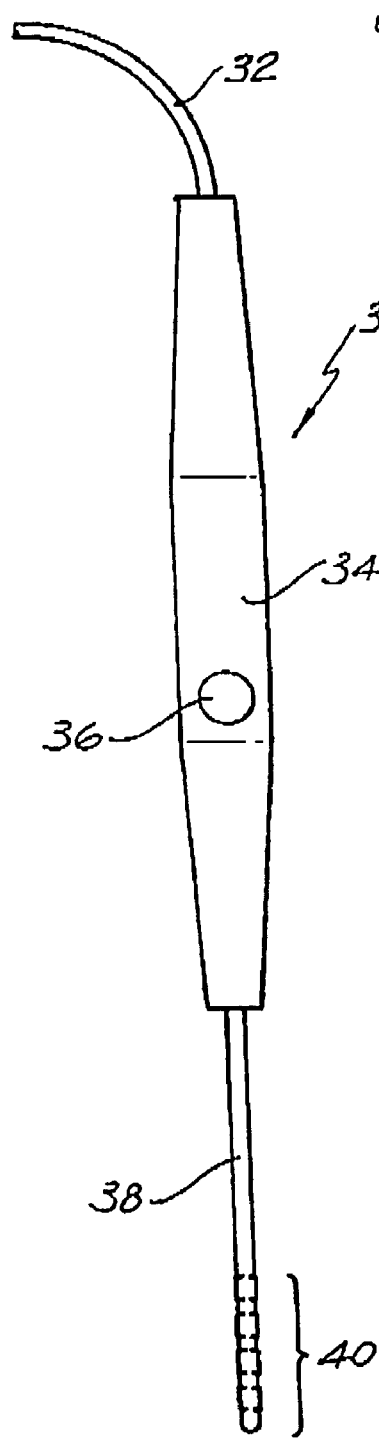
FIG. 3 is a bottom plan view of a hand-held surgical device incorporating an RF ablation probe according to the invention.
Figure 5:
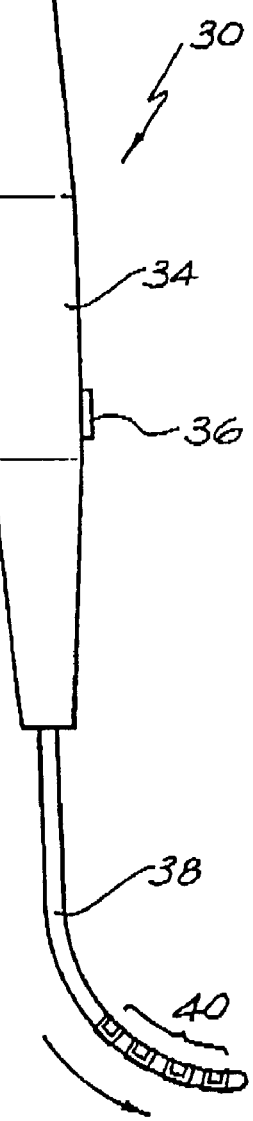
FIG. 5 is a right side elevation view of the device of FIG. 3.

As shown in FIG. 3, the handle of the hand-held device 34 also incorporates a button switch 36 which can be actuated to deliver RF energy to one or more of the electrodes 40 via internal conductors 42. While the upper surface of each electrode 40 is flat, a side elevation view of FIG. 5 illustrates that in this embodiment a number of thin legs are preferably provided on both longitudinal edges of the electrodes 40. Using such legs, the substantially flat electrode 40 on the upper surface of the probe body 38 can be crimped or otherwise fastened thereto. The terminal ends of the crimping legs shown in FIG. 3 are generally indicated by the bracket with reference numeral 40.

This embodiment of the invention may be practiced using crimping alone, or in combination with bio-compatible adhesives such as a two-component epoxy resin. The respective under-surfaces of the electrodes 40 can be adhered to the insulative body 38 using such an epoxy resin. The epoxy resin should have a suitable binding strength that remains stable between body temperature and 120° C., if crimping and other mechanical fastening techniques are to be avoided. In the light of the foregoing, it will be apparent to those skilled in the art that other methods of fastening or incorporating electrodes in an insulative body well-known to such persons can be practiced without departing from the scope and spirit of the present invention.

The electrodes 40 must be electrically conductive, and preferably are made of metal. Still further, in the embodiment shown, the electrodes 40 are made of stainless steel. However, it will be apparent to one skilled in the art that other materials having high electrical conductivity and capable of withstanding temperatures between room temperature and about 120° C. can be used without departing from the scope and spirit of the invention.

FIG. 5 indicates that the RF ablation probe 38, 40 can be bent, adapted, shaped or otherwise deformed or deflected as indicated by the arrow in the side elevation view. In particular, the distal end of the probe body 38 having the four electrodes 40 is curved downwardly relative to the position shown in the top plan view of FIG. 4. In this embodiment, the stainless steel electrodes 40 incorporated in the distal end of the probe 38 each preferably have dimensions of 4 mm×2.5 mm, with a spacing of 4 mm between each pair of electrodes 40. Thus, the electrodes 40 have a thin, flat, substantially rectangular form. The malleable tip may preferably be 3 to 6 cm in length. However, other sizes and shapes of electrodes and spacing therebetween may be practiced without departing from the scope and spirit of the invention. Smaller electrodes with equally smaller spacing therebetween may be practiced, thereby offering increased bendability to the probe structure. For example, small square electrodes of 2.5×2.5 mm with inter-electrode distances of 2.5 mm or less may be practiced.

Figure 6A:
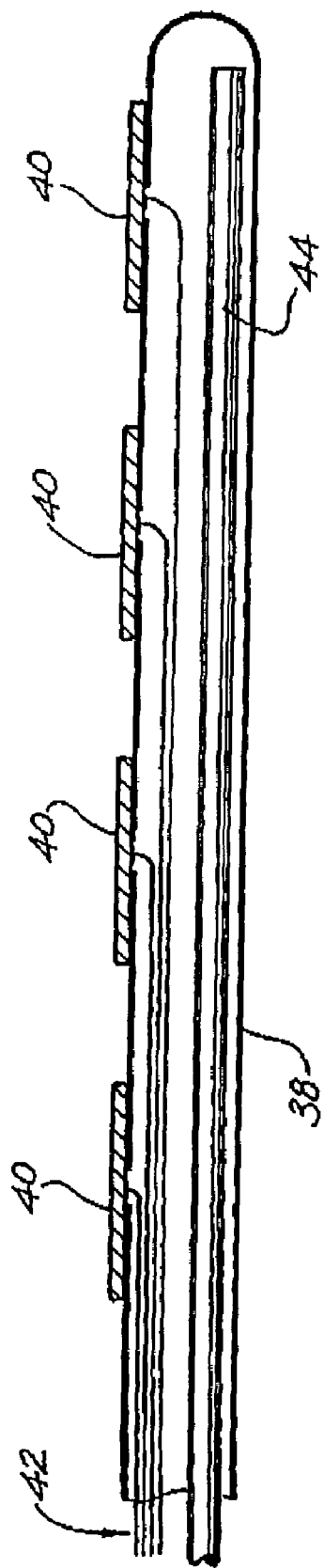
FIGS. 6A and 6B are sectional, side elevation and cross-sectional, front elevation views of the RF ablation probe according to the embodiments of the invention, generally, and in particular the embodiment shown in FIG. 3.
Figure 6B:
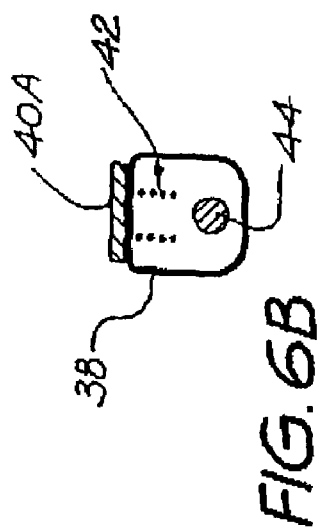

FIGS. 6A and 6B are sectional side elevation and cross-sectional front elevation views, respectively, of the probe 38, 40 of FIGS. 3 to 5. To simplify the drawing, the crimping legs extending from each of the four electrodes 40 are not illustrated. The malleable member is a copper core 44 included within the insulative body 38 that runs lengthwise along the longitudinal extent of the probe 38. Arranged along the upper flat surface of the insulative body 38 are four rectangular electrodes 40. Preferably, each flat electrode 40 has a thermocouple or other temperature sensing device connected therewith for measuring the temperature of the electrode 40. Thus, one of the electrical leads 42 may be made of a metal conductor such as stainless steel, while the other lead comprises a thermocouple, such as nickel. Alternatively, a thermistor can be connected to the electrode 40 as the temperature sensing device. In each case, the electrical lead(s) 42 is fixedly connected to a respective electrode 40, and this is preferably done by spot welding. As indicated in FIG. 6B, the upper surface of the insulative probe body 38 is preferably flat and the electrodes 40 (e.g., 40A) are likewise flat.

This embodiment of the invention is made by affixing, preferably using an epoxy resin, the flat electrodes 40 to an upper surface of the insulative plastics or rubber-like, hollow tubing 38 and then spot welding each pair of electrical conductors 42 to the respective electrode 40. This welding also serves to increase the mechanical strength binding the electrodes 40 to the body 38. The malleable member or core 44 is provided in the hollow interior of the tubular body 38. The crimping legs shown in FIGS. 3 and 5, are then crimped to securely bind the elements 38, 40, 44 together. In an alternative configuration, prior to crimping of legs, the hollow interior containing the electrical leads 42 and the malleable core 44 can be filled with an insulative, rubbery material such as SILASTIC (trade mark) to form a solid matrix.

While the first embodiment of the invention has been described with reference to electrodes formed and bound to the probe body by affixing using adhesive and crimping, it will be readily apparent to one skilled in the art that other techniques can be practiced without departing from the scope and spirit of the invention. Further, rather than affixing or crimping the electrode to an insulative body, where the body itself provides the insulation between electrodes, the insulative portion(s) may be applied separately by, for example, spray coating and silicon layer.

USE OF THE FIRST EMBODIMENT

FIGS. 7A to 7D illustrate an exemplary use of the malleable ablation probe 38, 40 to produce linear lesions. To septate an interior surface of the right atrium 96, a small cut 94 is made into the myocardial tissue. A surgeon then illuminates the aperture using a light 92 and observes the interior surfaces of the chamber. Having observed the surface to be ablated, the surgeon shapes, bends or otherwise deforms the RF ablation probe 38, 40 so that the malleable tip containing the electrodes 40 conforms with the surface to be ablated. The surgeon can test fit the tip and remove it for minor shape adjustments until a satisfactorily complementary fit is achieved between the tip electrodes and the tissue surface.

Figure 7A:
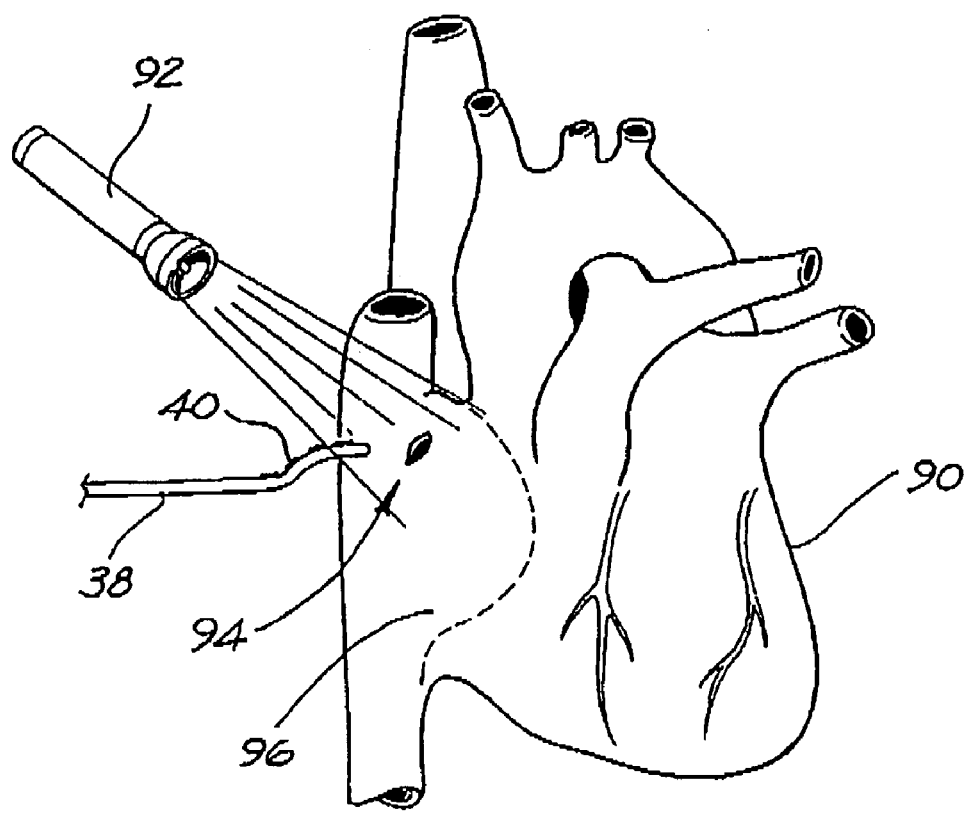
FIGS. 7A to 7D illustrate the use of the RF ablation probe shown in FIG. 3 to septate myocardial tissue.
Figure 7B:
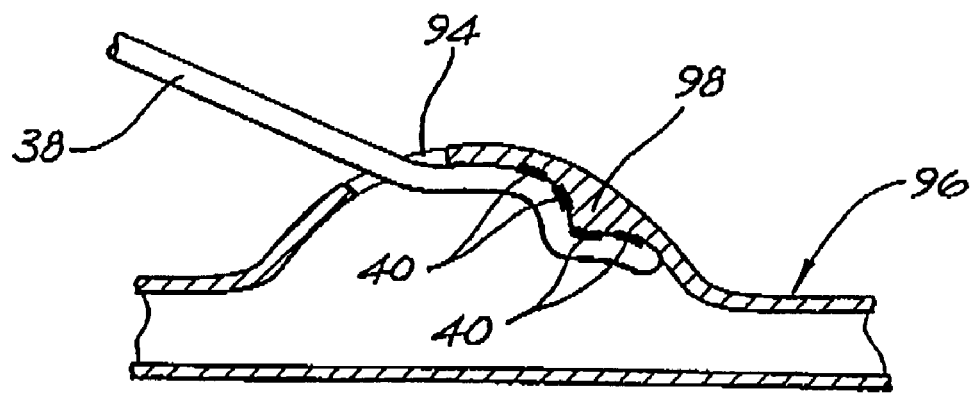
Figure 7C:
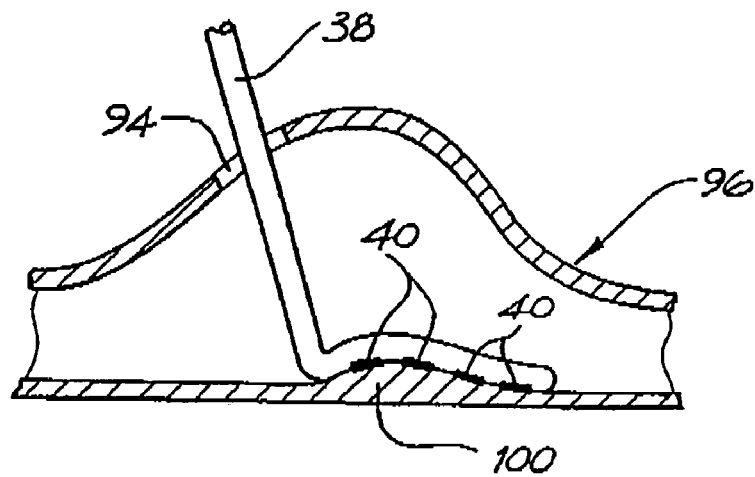

FIG. 7B illustrates a reverse "S" shape formed by the RF ablation probe 38, which is inserted via the aperture 94 into the atrium 96. The upper surface of the probe 38 containing the electrodes 40 is bent to conform with the contoured inner surface of the atrium 96 and in particular, to take account of the protruding, irregularly shaped mass of tissue 98. In this manner, a full, solid contact is formed between the flat electrodes 40 and the tissue to be ablated. FIG. 7C likewise illustrates an irregularly shaped surface 100 formed in the opposite wall of the atrium. The probe 38 is shown formed into an exaggerated "L" shape with a bend formed in the lower leg of the "L" to conform with the protruding surface 100.

Figure 7D:
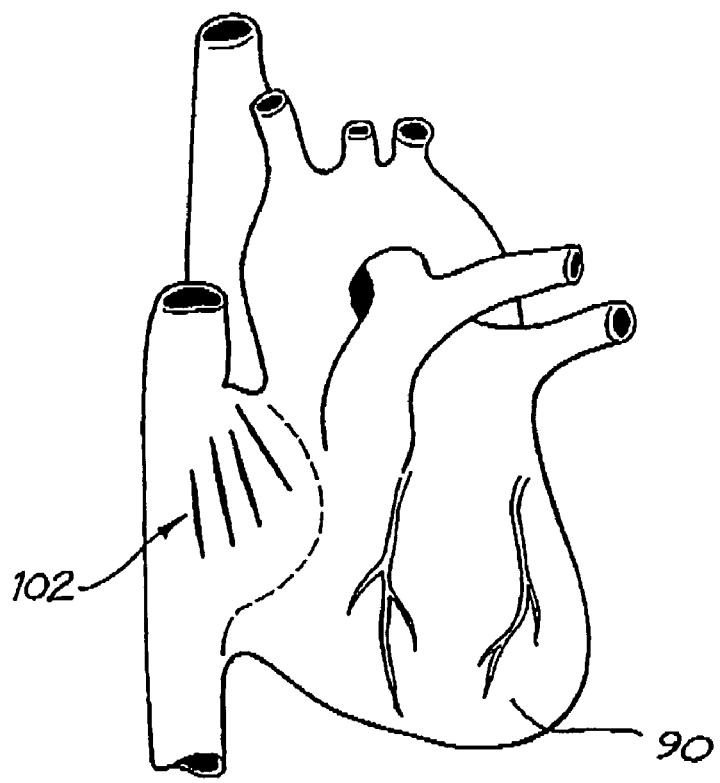

In this manner, a number of elongated lesions can be formed within the interior surface of the atrium 96, as indicated schematically by solid lines 102 in FIG. 7D. It will be appreciated by one skilled in the art that the lines 102 represent linear transmural lesions in the interior surface of the atrium 96 as produced in accordance with the use of the malleable probe 38 to ablate endocardial tissue as shown in FIGS. 7B and 7C. Likewise, the bendable, adaptable RF ablation probe can used to produce elongated, thin lesions from the epicardial surface.

SECOND EMBODIMENT

Figure 8:
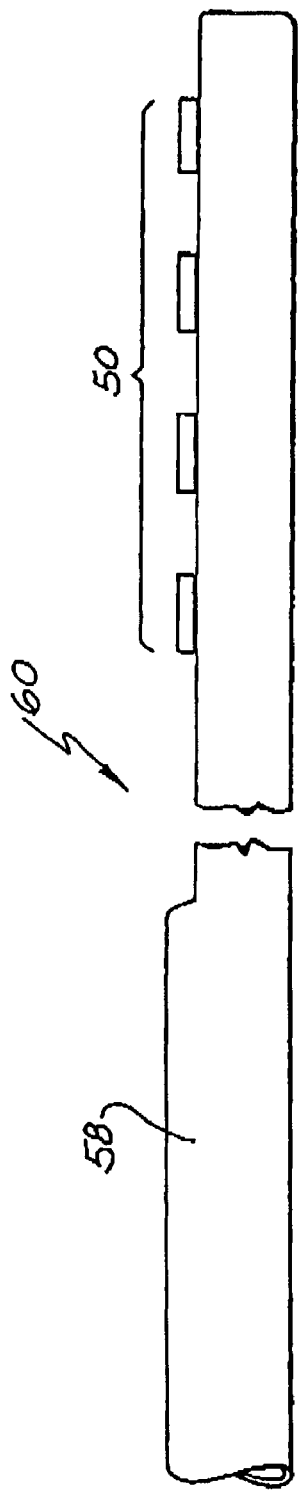
FIGS. 8, 9 and 10 are side elevation, top plan and cross-sectional front views of a second embodiment of an RF ablation probe according to the invention.
Figure 9:
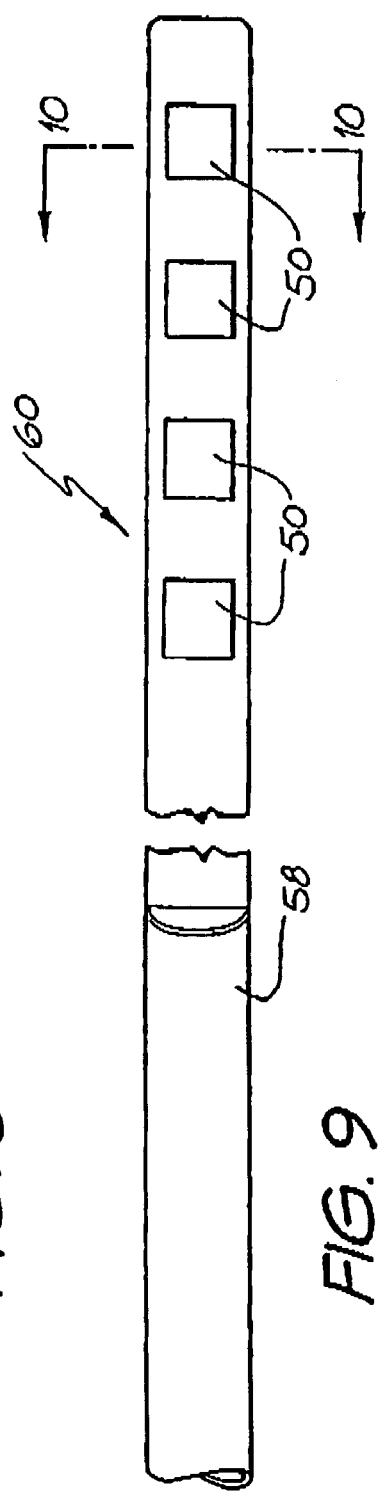
Figure 10:
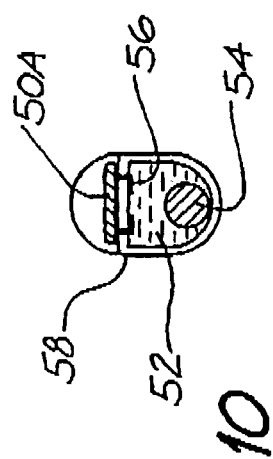

FIGS. 8 to 10 illustrate side elevation, top plan and cross-sectional front elevation views of an RF ablation probe according to the second embodiment of the invention. The RF ablation probe 60 comprises a hollow, substantially tubular body 58 made of teflon plastic, a number of flat, conductive electrodes 50, and a malleable core 54 (not shown in FIGS. 8 and 9) contained within the centre of the thermally and electrically insulative body 58. In particular, the teflon body 58 has a relatively rigid yet bendable structure and is capable of being permanently formed to have a particular shape. As indicated in FIG. 8, the upper surface of the distal end of the tubular body 58 is crimped to produce a flat surface. The electrodes 50 are arranged on the flat upper surface, and again are separated by thermally and electrically insulative material.

The electrodes 50 have a like construction to those described hereinbefore with reference to the first embodiment. The flat upper surface of the tubular body 58 provides a complementary surface to that of the underside of each of the electrodes 50 and thereby ensures a solid connection between the two surfaces. Adhesive such as a bio-compatible epoxy resin is preferably used to bond the undersurface of each electrode 50 with the upper flat surface of the tubular body 58.

Still further, it is preferable to weld or incorporate prongs or teeth 56 capable of being bent to the under surface of each electrode 50. With reference to FIG. 10, such prongs or teeth 56 rigidly connected to the under surface of an electrode 50 can be used to puncture the tubular body 58 when the electrode 50 is pressed into contact therewith. Once the teeth or prongs 56 are inserted through the tubular body 58 so that the electrode 50 is in direct contact with the surface of the tubular body 58, the teeth or prongs 56 are bent within the interior of the body 58 to rigidly interconnect the electrode 50 and the tubular body 58. This may be done in addition to applying adhesive between the lower surface of the electrodes 50 and the tubular body 58.

With a malleable core 54, preferably made of copper, inserted within the internal cavity of the tubular body 58, the internal cavity may then be filled with a sufficiently bendable matrix 52. Preferably, a rubber like spongy matrix 52 made of SILASTIC (trade mark) or the like is used. It will be apparent to a person skilled in the art, however, that other bendable materials can be used without departing from the scope and spirit of the invention.

The RF ablation probe 60 according to the second embodiment may be practiced in numerous ways including the exemplary manner described hereinbefore with reference to FIGS. 7A to 7D. The second embodiment is advantageous in that it provides a linear arrangement of flat electrodes capable of producing an elongated lesion in a malleable probe structure having a memory function. In particular, the probe may be bent or shaped to conform with an irregular or contoured surface and retain such shape.

THIRD EMBODIMENT

FIGS. 11 to 13 illustrate an RF ablation probe 70 according to a third embodiment of the invention. Again, a number of flat electrodes 80 are arranged at predetermined spaces on a top surface of an elongate probe body 82. The body of 82 of the probe is tubular and preferably made of a rubber or soft plastic materials, such as SILASTIC, which is thermally and electrically insulative. Electrical conductors or leads connected to each electrode 80 are not shown in FIGS. 11 to 12 to simplify the diagram.

In this embodiment, rather than having an internal malleable core, a rigid, pre-formed or shaped insert member 84 is inserted into the internal cavity of the tubular body 82 at its distal end to thereby give the probe 70 a corresponding pre-formed shape. The insert member 84 in this example has an S-shape. In FIGS. 11 and 13, the pre-formed, rigid, cylindrical insert member 84 is preferably made of stainless steel or a rigid plastic body and can be inserted into the interior cavity of the body 82 to thereby give the probe 70 a corresponding S-like shape. For example, pre-formed insert members 84 can be made to complement the form of known tissue bodies. Alternatively, the insert member 84 can take the form of a deformable material, allowing a surgeon to customise its bent shape prior to use.

Using such pre-defined inserts 84, the flexible probe 70 is provided with a pre-determined shape so as to conform the probe 70 to that shape. The probe 70 can be used to produce linear lesions.

FOURTH EMBODIMENT

Figure 14:
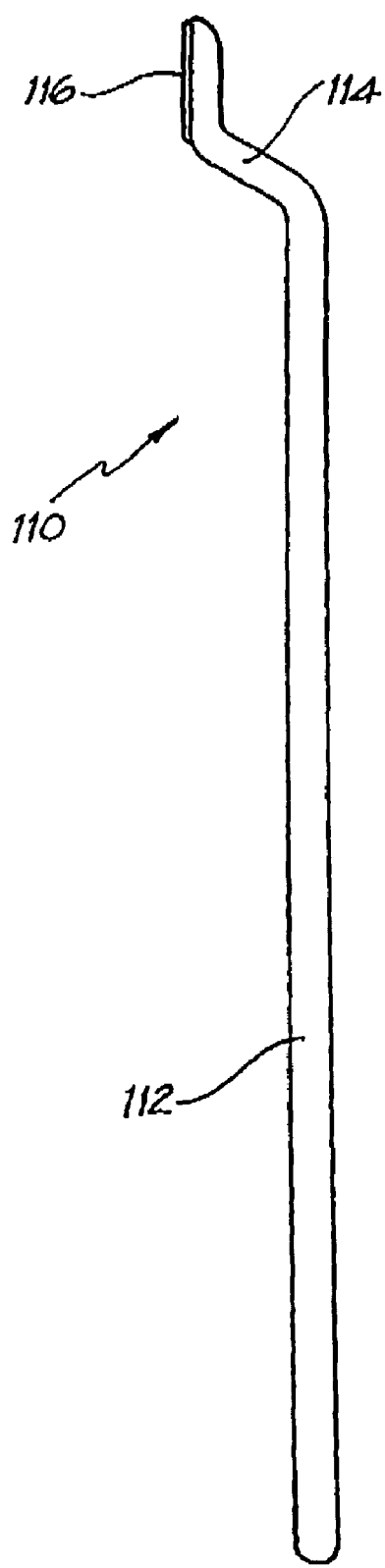
FIGS. 14 and 15 are side elevation and top plan views of a fourth embodiment of an RF ablation probe according to a the invention.
Figure 15:
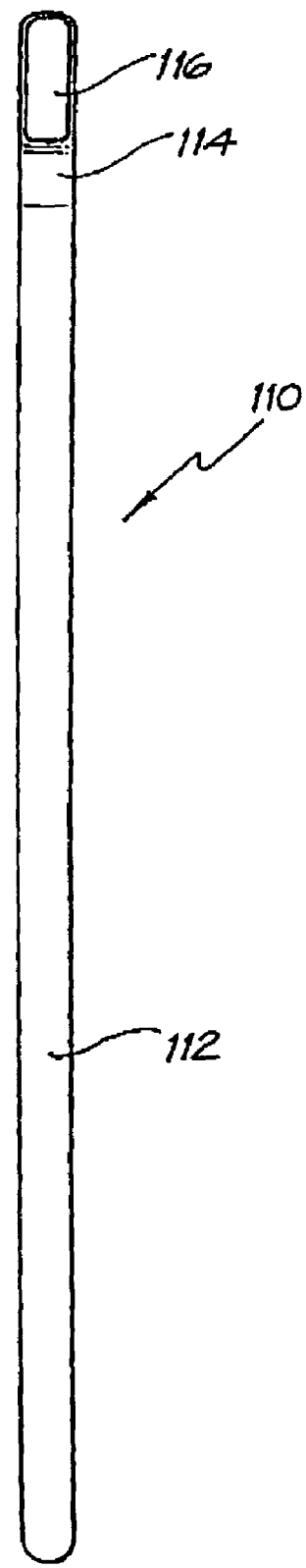

FIGS. 14 and 15 illustrate a forth embodiment of an RF ablation probe 110 for producing elongated, thin linear lesions in a tissue. In this embodiment, the probe 110 consists of a solid, rigid body 112, preferably having an S or L-shaped terminal region 114 at the distal end. The upper surface of the distal end 114 of the probe 110 is provided with a flat surface. An elongated, flat conductive electrode 116 is provided on the flat surface, and preferably has a rectangular shape.

The body 112 of the probe 110 is preferably made of a rigid material such as metal coated with an appropriate insulative material. Alternatively, the probe can be made of plastic and contain electrical conductors preferably internally connected to the electrode 116. RF energy can be delivered to tissue in contact with the electrode 116. Further, the temperature of the electrode in contact with tissue can be sensed using a thermocouple or other temperature sensing device connected therewith. Still further, the electrode 116 may be used for detecting or mapping electrical activity in the tissue contacting the electrode 116.

This probe 110 can be used to produce linear, elongated transmural lesions in endocardial and epicardial tissue, and is able to apply or transfer significant pressure between the electrode 116 and the tissue in contact therewith. This ensures that a solid contact is formed with the tissue for delivery of RF energy to the tissue.

Only a small number of embodiments of the invention has been described. Changes and/or modifications obvious to one skilled in the art in view of the specification can be made without departing from the scope and spirit of the invention.

The invention claimed is:

1. A probe for ablating tissue, comprising:
   a tubular body of a bendable material defining an elongate cavity;
   a plurality of flat electrodes linearly arranged along the longitudinal extent of said tubular body;
   insulative portions separating said electrodes from each other;
   a plurality of electrical conductors, at least one of which is connected with each respective one of said plurality of electrodes; and
   an insert member having a predefined shape for insertion into the elongate cavity of said tubular body, wherein said tubular body conforms to the predefined shape upon insertion of the insert member into the elongate cavity.

2. A probe according to claim 1, further comprising a plurality of temperature sensing devices each of which is connected to a respective one of said plurality of electrodes.

3. A probe according to claim 2, wherein at least two conductors of said plurality of conductors are connected to each of said electrodes, and wherein one of said conductors comprises a thermocouple as said temperature sensing device.

4. A probe according to claim 1, wherein one or more prongs are connected with each of the electrodes, wherein said one or more prongs is used to puncture said body and is capable of being bent.

5. A probe according to claim 1, wherein said body is made of insulative material.

* * * * *